United States Patent [19]

Shibasaki et al.

[11] 4,441,813
[45] Apr. 10, 1984

[54] APPARATUS FOR DETECTING PINHOLES IN CANS

[75] Inventors: Kyuichi Shibasaki; Hideo Kurashima, both of Yokosuka, Japan

[73] Assignee: Toyo Seikan Kaisha, Ltd., Tokyo, Japan

[21] Appl. No.: 242,496

[22] Filed: Mar. 10, 1981

[51] Int. Cl.³ ............................................. G01N 21/90
[52] U.S. Cl. .................. 356/237; 250/223 B
[58] Field of Search ................ 356/237, 239, 240; 250/223 B; 209/588

[56] References Cited
U.S. PATENT DOCUMENTS 3,395,285  7/1968  Scanlon et al. .................... 250/548
3,416,659  12/1968  Linderman et al. ................. 209/588

Primary Examiner—Vincent P. McGraw
Assistant Examiner—L. A. Dietert
Attorney, Agent, or Firm—Jordan & Hamburg

[57] ABSTRACT

An apparatus for detecting pinholes in cans comprising a dark box consisting of a light seal plate and a window, a photodetector detecting electrically the outer penetration of light, and light sources disposed around the can. The light seal plate has a groove for receiving an open end of a can therein and is of a hardness greater than that of the can. The groove of the light seal plate communicates with a trap. The surface of the groove is black non-luster.

16 Claims, 12 Drawing Figures

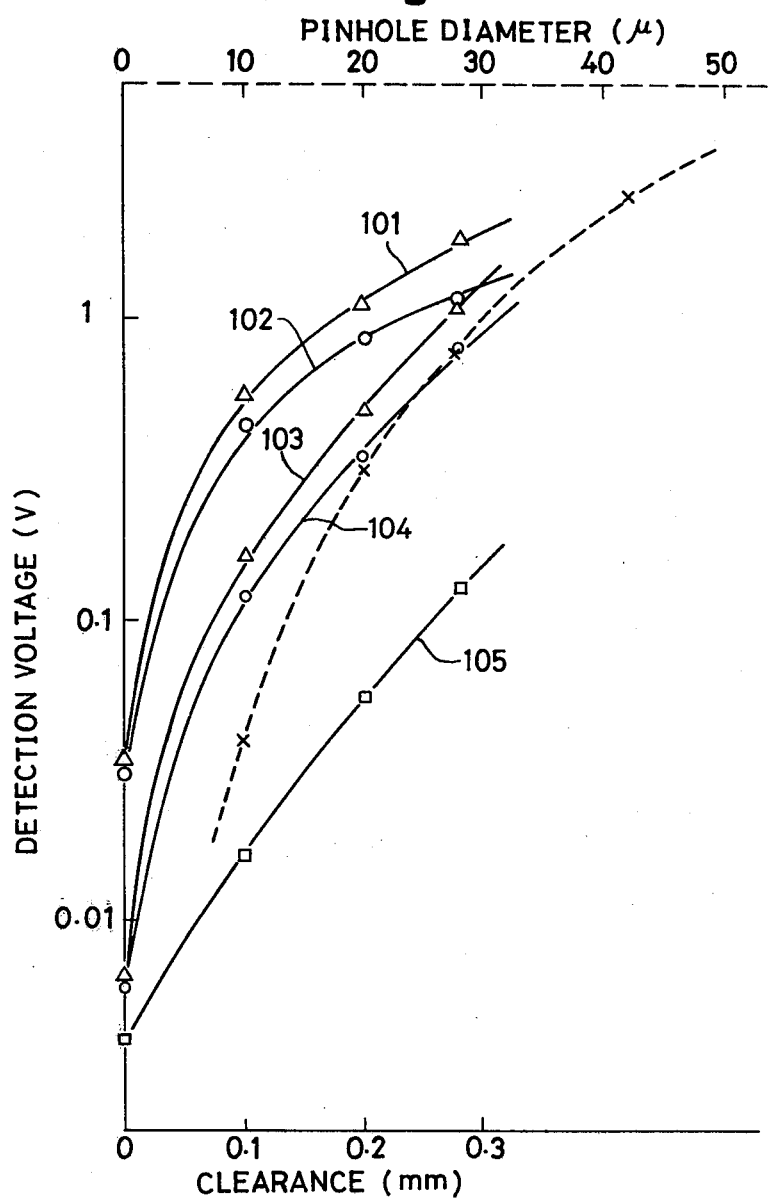

APPARATUS FOR DETECTING PINHOLES IN CANS

BACKGROUND OF THE INVENTION

This invention relates to an apparatus for detecting pinholes in cans and in particular to an improvement of apparatus for detecting pinholes in cans by radiating light toward the cans.

Cans made of thin metal plates, such as tin, tinfreesteel and aluminum plate are broadly used as containers for hermetically filling with refreshments, pharmaceuticals, cosmetics, and other products for daily life. In these kinds of cans, pinholes or cracks (cracks are referred to as pinholes below) are caused from failure in the can manufacturing line and the mixture of nonmetals into the can materials. As a result, the problem of leakage out of the cans arises. Therefore it is necessary to detect pinholes in the can manufacturing line.

The air pressure method and the transit light method are known as conventional pinhole detection methods. The pinhole detection apparatus using the air pressure method detects changes in the internal pressure of the cans by a pressure detector or diaphram gauge which keeps the internal pressure high or low, and measures the internal pressure of cans of which the ends are sealed with rubber packing. This air pressure method is suitable to detect pinholes in the band seam (double seam) portion of the cans or the junction of the body and the bottom of the cans and leakage in the band seam (double seam) portion due to the failure of the windingup seam. But defects as described below are found in this air pressure method. That is, the internal pressure variation resulting from pinholes and other reasons is generally very slow in the variation speed, therefore it requires a long detection time. For example, in case a can having 200 cc capacity has a pinhole of 50μ diameter, it requires a minute for certain detection. At this time, air pressure of 1 kg/cm$^2$ is given as the initial pressure, and then pressure reduction of 50 g/cm$^2$ must be detected. As will be apparent from this description, in the conventional air pressure method, a number of can detections require much labor and time.

Also, in the air pressure method, the opening end of the cans must be steadily pressed to the rubber packing to maintain high or low pressure within the cans. As a result, the rubber packing frequently blocks up pinholes in a processing flange of the can opening. It is very difficult for this method to detect pinholes in the adjacent opening end.

In addition, coatings or print inks cover the pinholes having diameters of 100μ or less in the cans in which the inside and the outside thereof are coated or printed for cosmetic or prevention of corrosion. This makes the pinholes detection difficult when the detection is made.

On the other hand, the transit light method detects pinholes by directing irradiation light to the outside of the cans and then by detecting light passing through pinholes into the interior of the cans. This method is preferably suitable to detect pinholes in cans having no band seam (double seam) portion. Namely, the transit light method is available to detect pinholes since the ratio of DI (Drawing and Ironing) cans manufactured by the drawing and ironing processing is increasing these days. In the DI cans the body and bottom are incorporated in one by the drawing. The conventional pinhole detection apparatus with the light detection method is known in U.S. Pat. No. 3,416,659, and a schematic representation thereof is shown in FIG. 1.

In FIG. 1, an opening end (10a) of the DI can (10) tightly contacts a light seal plate (14) of a dark box (12) with the DI can (10) standed upside down. The box (12) has a window (12a) for communicating with the interior of the can (10). A vacuum pump (not shown) reduces the internal pressure within the box (12) and the can (10) through an exhaust opening (16) provided with a side wall of the box (12). As a result, the opening end (10a) and the light seal plate (14) are tightly contacted with each other by the difference between the internal and the atmospheric pressures. The light seal plate (14) is of opaque rubber packing. An engagement of the opening end (10a) in the light seal plate seals light. Light sources (18) are above and around the can (10) which is exposed to both the direct light from the sources (18) and the reflected light from a cylindrical reflector (20) around the sources. A photo detector (22) provided within the box (12) detects light passing through pinholes from the light sources (18) and then converts its light into an electrical output (100) through a signal circuit (not shown). Thus, pinholes in the can are detected.

According to the conventional apparatus of FIG. 1, light from the light sources (18) through pinholes into the interior of the can (10) reaches the photo detector (22) directly or reaches it with light repeatedly scattered and reflected within the inside wall of the can (10). The photo detector (22) is capable of detecting pinholes anywhere on the can (10) by the optical integral action of the reflected, scattered light, and therefore possibly acquires the high sensitive pinhole detection action.

However, in this conventional apparatus, leaked light out of the seal portion between the opening end (10a) of the can (10) and the light seal plate (14) produces detection noises. To reduce the amount of this leaked light, the reduced internal pressure provided within the box (12) and the can (10) is made to tightly contact the opening (10a) with the light seal plate (14). As a result, wear of the light seal plate (14) becomes extreme. Generally, in the conventional apparatus, the can (10) is detected with the condition that the flange is formed in the opening end (10a), in other words, the end surface of the opening end (10a) is rounded. But even with this roundness the opening end (10a) results in extreme wear of the light seal plate (14) of the rubber packing. In general, a side use of two to three weeks and both sides use of about six weeks make frequent replacements of the parts, and make maintenance of the detection apparatus difficult. In addition, the use of the easily worn light seal plate (14) results in error detections.

FIG. 2 shows other samples with respect to the light seal plate (14) of the conventional rubber packing. These samples illustrate the structures for reducing the leaked light out of the tight contact portion between the opening end (10a) and light seal plate (14). FIG. 2A shows a dish-shaped concave portion provided on the tight contact surface with the opening end (10a), which makes it easy to receive the opening end (14). But, on the contrary, its structure does not fit nicely the opening end (10a) with the light seal plate (14), therefore both must be strongly pressed to each other. FIG. 2B shows a funnel-shaped light seal plate (14). In this other example, in the same way as FIG. 2A, unfitness of the opening end (10a) to the light seal plate (14) increases the amount of leaked light. Still further, FIG. 2C shows a ⊐-shaped sectional light seal plate (14) capable of tightly contacting the opening end (10a) with the light seal plate (14) with slight contact pressure. But, too much contact pressure and irregularity of axis position of the can to the light seal plate (14), produce uneven deformation of the light seal plate (14), and hence a large amount of leaked light occurs. Also it requires much time to adjust contact pressure or contact position. Further, the pressure or changes of the contact position must be managed.

Also, in the conventional apparatus, in the same way to the air pressure method, pinholes are covered with coatings or printing ink. Especially, detecting pinholes of diameters of 100μ or less become extremely difficult. Practically, the cans having pinholes covered with coatings or print inks keep good air-tightness for only a few days. In most cases, pinholes produce leakage after a week and remarkably increase the ratio of the defective cans. In particular, the defective cans having substances have a practical influence on common consumers. This is a very big problem.

As will be apparent from the above description, pinholes are preferably detected before the coating or printing operation. But as well known, in the DI processing operation, the drawing or ironing processed DI can is made a necking and flange processing in the opening end. The shape remains as it was before the rounded end surface processing in the can end is made. The trimmed end surface has a width such as about 0.17 mm, which is very thin. As a result, when the opening end (10a) tightly contacts the light seal plate (14), the light seal plate (14) is remarkably worn or is easily broken in a particular case. Therefore, it is impossible to detect pinholes before coating or printing.

This invention relates to improvement of the above conventional apparatus.

An object of this invention is to provide a can pinhole detection apparatus with very high detection accuracy which remarkably elongates maintenance and exchange term of the light seal plate or has no necessity of replacements of the light seal plate by improving the light seal plate.

An object of this invention is to provide a can pinhole detection apparatus for precisely detecting defective cans without attenuating the transit light into the interior of the can.

Another object of this invention is to provide a can pinhole detection apparatus in which the maintenance is made with ease and the light seal plate with wear resisting property has a long replacement life.

Another object of this invention is to provide a can pinhole detection apparatus having the light seal plate with a conical-shaped introduction, which makes it easy to insert an opening end of the can therein.

A further object of this invention is to provide a can pinhole detection apparatus in which a slight pressure is given to the can in order to easily close the opening end of the can.

A further object of this invention is to provide a can pinhole detection apparatus in which the light seal plate has a groove for accepting the open end of the can therein and is of harder material than that of the can.

A still further object of this invention is to provide a can pinhole detection apparatus in which the groove surface of the light seal plate is treated with specific materials to attenuate the reflection of light.

To achieve the above objects, this invention is characterized in that a light seal plate has a groove for accepting an open end of a can and is of very hard material in a pinhole detection apparatus. The apparatus comprises a dark box having a window through which an interior of the can communicates with the light seal plate shutting incidental light by tightly contacting the open end of the can therewith, a photo detector electrically detecting the incidental light within the dark box and light sources.

The above and other advantages of the invention will become more apparent in the following description and the accompanying drawings.

BRIEF DESCRIPTION OF THE DRAWINGS

FIG. 9 is a view of graphs showing a function of this invention; and

DESCRIPTION OF THE PREFERRED EMBODIMENTS

Figure 1:
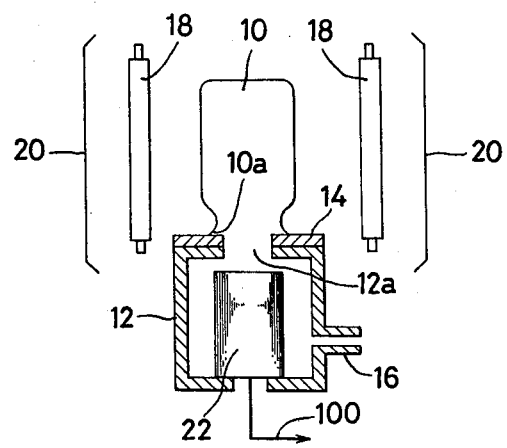
FIG. 1 is a sectional view of the principal parts showing a schematic structure of a conventional pinhole detection apparatus.
Figure 2A:
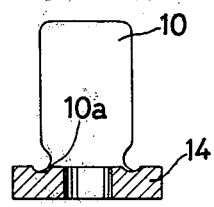
FIGS. 2A, 2B and 2C are sectional views of the principal parts showing other examples of conventional light seal plates respectively.
Figure 2B:
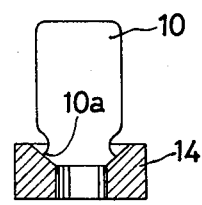
Figure 2C:
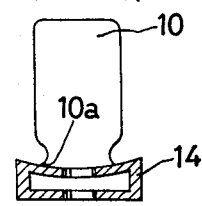
Figure 3:
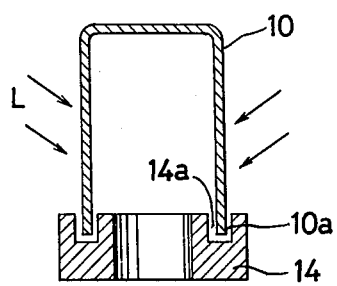
FIG. 3 is a sectional view of the principal parts showing a pinhole detection apparatus of this invention.

FIG. 3 shows a structure of a light seal plate (14) suitable for this invention. The light seal plate (14) has a groove (14a) for accepting an open end (10a) of a can (10) therein. The open end (10a) of the can (10) is inserted to the bottom of the groove (14a). The light seal plate (14) is composed of harder materials than that of the can, and therefore is not damaged by contacting the can (10). The harder materials are, for example, superhard substances, sintered ceramics, hard-facing-treated steel and so forth. The hard facing treatments are preferably, for example, nitriding treatment and the metal or ceramics spray coating treatment.

This invention is characterized in, as above described, that the light attenuation action of the groove (14a) reduces the amount of leaked light from between the opening end (10a) and the light seal plate (14) to the degree that the amount of leaked light is neglected, when the open end (10a) of the can (10) is inserted into the groove (14a) provided on the light seal plate (14). That is, this invention decreases effectively the amount of leaked light while permitting the outer entry of light without perfectly shutting the outer entry light by a clearance between the open end (10a) of the can (10) and the light seal plate (14).

Figure 4:
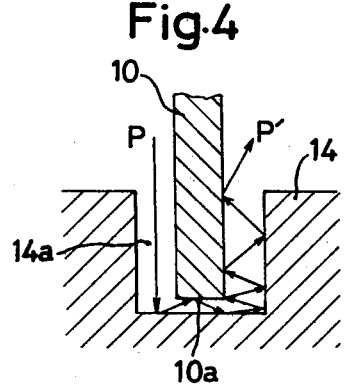
FIGS. 4 and 5 are explanatory views showing the leakage light attenuation action of the apparatus in FIG. 3.

FIG. 4 shows the leaked light attenuation action of the groove (14a) of the light seal plate (14). As will be apparent from FIG. 4, outer light (P) enters into the clearance between the can (10) and the groove (14a). The outer light (P) is reflected at right angles to the bottom of the groove (14a) and leaked into the interior of the can from the clearance between the opening end (10a) and the bottom of the groove (14a). This leaked light is further directed to 90° with light repeatedly reflected inside the bottom of the groove (14a). Accordingly, the outer light (P) has a total of twice a 90° reflection and then enters into the interior of the can (10). The amount of leaked light is remarkably attenuated in every reflection. Therefore, the amount of leaked light (P') reaching the interior of the can (10) is much smaller than that of light passing through pinholes, and has no influence on the detection. Basically, when the reflectivity of 90° direction in the groove (14a) is defined as $\eta$, leaked light (P') is expressed as $P'=\eta^2 \cdot P$. As will be apparent from this expression, a few reflections attenuate remarkably the amount of the leaked light (P'). The smaller width and greater depth of the groove (14a) makes efficiency of the attenuation action high. Width and depth of the groove (14a) are preferably determined by experiments according to width and insertion operation of the can (10).

Figure 5:
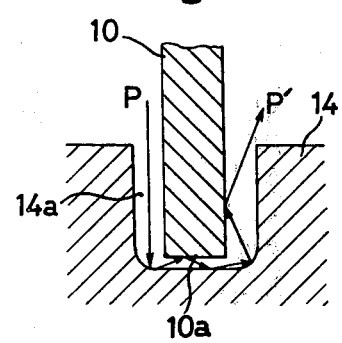
Figure 6:
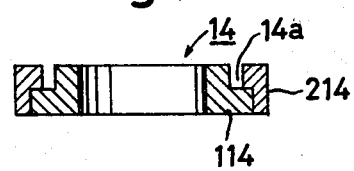
FIG. 6 is a sectional view showing another example of a light seal plate according to this invention.

In this invention, it is favorable that the bottom end of the groove (14a) provided on the light seal plate (14) is processed at right angles. For example, as illustrated in FIG. 5, roundness of the bottom edge angle of the groove (14a) makes it easier for outer light (P) to enter into the interior of the can (10) with a few numbers of reflections and then to enter its a-few-numbers-of-reflections light (P') into the interior of the can (10). Accordingly, the groove (14a) with such roundness limits the attenuation efficiency of the amount of the leaked light, therefore the edge of the groove (14a) must be precisely processed to further effect this invention. Generally, there are so many cases that roundness occurs in the edge when the groove is directly processed in the light seal plate (14). To prevent occurrence of roundness, in this invention and as illustrated in FIG. 6, the light seal plate (14) is a double structure one in which the grooves (14a) with the good edge is formed by combining the first light seal plate (114) with the second (214) and bonding them.

Figure 7:
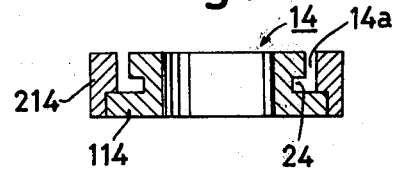
FIG. 7 is a sectional view showing a further example of a light seal plate according to this invention.

In addition, FIG. 7 shows another embodiment of this invention. The first light seal plate (114) has a trap (24) communicating with the groove (14a) and can acquire good light attenuation action.

Figure 8:
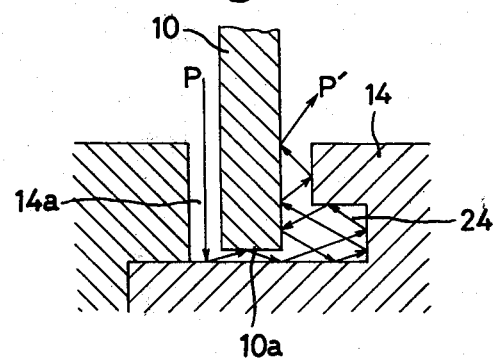
FIG. 8 is a explanatory view showing the leakage light attenuation action of the device in FIG. 7.

FIG. 8 shows the light attenuation effect of the trap (24) in the embodiment of FIG. 7. The outer entry of light from the clearance between the opening end (10a) and the groove (14a) into the trap (24) is greatly attenuated with repeated reflections and then enters into the interior of the can (10). Accordingly, the embodiments in FIGS. 7 and 8 can get the attenuation action in combination of both the groove (14a) and the trap (24), and remarkably limits the amount of the leaked entry light (P') into the interior of the can (10).

In each of such embodiments, the groove (14a) is formed in the light seal plate (14) by a cutting operation. Therefore the metallic luster of the surface of the groove (14a) makes the coefficient of reflection comparatively high. But in this invention, throwing black non-luster on the surface of the groove (14a) makes the coefficient of reflection low. To obtain it, in this invention, the groove (14a) is constituted of black sintering ceramic, which reduces the amount of leaked light entering into the interior of the can (10).

FIG. 9 shows characteristics of experiments to explain the effects of this invention. Ten multiplier phototubes with amplification degree of $10^6$ were used as the photo detector and supplied 1000 volts. Ten flourescent lamps of 50 Hz, 100 volts and 6 watts as the light source were provided around the can. At this time, the output from the photo detector was amplified to 500 times its origin and passed through the 1:1 band pass filter (central frequency 100 Hz), then the maximum amplitude value of signal (defined as the detection voltage) from the filter was detected. In FIG. 9, the broken line shows a characteristic of the detection voltage to pinhole diameters with the outer light perfectly blocked. As will be apparent from the broken line in FIG. 9, pinholes of $40\mu$ and $10\mu$ diameters have respectively voltages of 2.2 volt and 40 millivolts.

The full lines in FIG. 9 show characteristics of the detection voltage on the basis of leaked light out of the light seal plate of this invention. In the can having no pinholes, the horizontal axis shows a distance between the opening end (10a) and the groove (14a) which is defined as clearance. The detection voltage characteristics of the leaked light to this clearance are shown in FIG. 9. As will be apparent from characteristics of each full line, with a 0 mm clearance or the opening end (10a) contacted with the bottom of the groove (14a) the detection voltage is very small. Also FIG. 9 shows that the light seal effect is abruptly decreased as clearance distance is increased. In characteristics (101) and (102) of FIGS. 3 and 4, grooves (14a) with a depth of 3 mm have widths of 0.45 mm and 0.35 mm respectively. The wall thickness of the cans (10) is 0.17 mm. As clear from characteristics (101) and (102), with the opening end (10a) of the can (10) contacted with the bottom of the groove (14a), and the amount of leaked light has a voltage of 30 millivolts. This value of the detection voltage is equal to that in a $10\mu$ pinhole completely covered with coating or painting materials. Under these conditions, pinhole detection is possible.

FIG. 9 shows characteristics (103) and (104) of the light seal plate (14) having the trap (24) shown in the embodiments of FIGS. 7 and 8. Under the same condition it is clear that the effect of the trap (24) is great from comparing the characteristic (101) with the (102).

In addition, FIG. 9 shows a characteristic (105) of the black non-luster inner surface of the groove (14a) from which it is understood that the black non-luster surface reduces remarkably the amount of leaked light.

The size of the groove (14a) of this invention is determined by the characteristics of FIG. 9. In general, the ratio of the amount of transit light through pinholes to leaked light out of the seal plate is between 1:5 and 1:10. To detect pinholes having diameters of $20\mu$ or above, for example, the groove (14a) has preferably a width of 0.33 mm and a depth of 3 mm and communicates with the trap (24).

Figure 10:
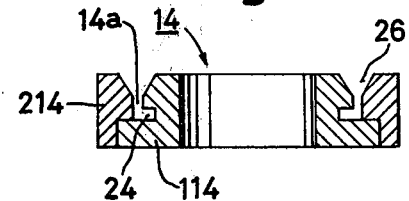
FIG. 10 is a sectional view showing a further example of the light seal plate according to this invention.

FIG. 10 shows a further embodiment of this invention, which seems to take after the embodiment of FIG. 7. It is characterized in that a conical introduction (26) is formed in the entrance of the groove (14a) which makes it easy to insert the opening end (10a) or the can (10) into the groove (14a).

As will be apparent from the characteristics of FIG. 9, it is much better that the opening end (10a) of the can (10) contacts the bottom of the groove (14a) and also the can (10) is pushed toward the bottom of the groove (14a) by hyaline push plates and others in order to prevent the can (10) from floating. Of course, this invention does not require a big pressure such as the contact pressure of the rubber packing in pushing the can (10) but requires only the prevention of the can floating.

As above described, this invention can utilize good materials with wear resisting property of high hardness materials in the light seal plate and elongate remarkably the maintenance and replacement term or remove it without wearing the light seal plate since the contact pressure is so small. Especially, not considering wear in on light seal plate, the pinhole detection is made with no roundness of the opening end processed before coating or printing, therefore the occurrence of the error detection resulting from covering pinholes with coatings or print inks can be certainly prevented. In addition, since pinholes are detected before coating and printing, the contamination of the mandrel in penetration of coatings or print inks through pinholes into the interior of the can is effectively prevented in the print work.

As above mentioned, this invention provides the pinhole detection apparatus which can be continuously used for a long time and is available to broadly apply inspection in various can manufacturing processing and other processes.

What is claimed is:

1. Apparatus for detecting pinholes in cans comprising dark box means for excluding ambient light, said dark box means having an interior and a window communicating with said interior, light seal plate means disposed at said window and adapted to cooperate with the end of a can to attenuate passage of light between said can and said light seal plate means as the interior of said can communicates with the interior of said dark box means through said window, photodetector means in said dark box means for detecting light entering into the interior of said can through pinholes in said can and for producing an electrical signal, and light source means adapted to be disposed externally of said can for radiating light onto said can, said light seal plate means comprising receiving groove means defining a receiving groove adapted to receive the open end of said can, said receiving groove including a trap groove in communication with said receiving groove and operable to attenuate outside light entering said receiving groove and passing into the interior of said can.

2. Apparatus according to claim 1, wherein said receiving groove has a bottom end and an open end, said open end of said can being inserted into said receiving groove through said open end of said receiving groove, said receiving groove having an annular configuration with an outer diameter and an inner diameter, said trap comprising an annular trap groove disposed adjacent to said bottom end of said receiving groove, said trap groove having an inner diameter less than the inner diameter of said receiving groove, whereby outside light entering said receiving groove is attenuated in passing through said trap groove to the interior of said can.

3. Apparatus according to claim 2, wherein said trap groove has an outer diameter equal to the inner diameter of said receiving groove.

4. Apparatus according to claim 2, wherein said trap groove is spaced from said open end of said receiving groove.

5. Apparatus according to claim 2, wherein said trap groove has a bottom end which is coplanar with the bottom end of said receiving groove.

6. Apparatus according to claim 5, wherein said trap groove has an outer end spaced from and parallel to said bottom end, said outer end of said trap groove being disposed between said bottom end and open end of said receiving groove.

7. Apparatus according to claim 1, wherein said light seal plate means is made of a material having a hardness greater than the hardness of the material from which the can is made.

8. Apparatus according to claim 7, wherein said light seal plate means comprises ceramic material.

9. Apparatus according to claim 7, wherein said light seal plate means comprises a steel material which has been subjected to nitriding.

10. Apparatus according to claim 1, wherein said receiving groove has an entrance portion through which the can end is introduced into said receiving groove, said entrance portion having a frusto-conical configuration.

11. Apparatus for inspecting open-ended cans for defects, the combination comprising a light sealing means adapted to be disposed at the open end of said can for attenuating light attempting to enter the open end of said can, and light detector means adapted to be disposed about the outside of said can for detecting light penetrating through defects in the can, said light sealing means comprising receiving groove means defining a receiving groove for receiving the open end of the can, said receiving groove including a trap groove in communication with said receiving groove and operable to attenuate outside light entering said receiving groove and passing into the interior of said can.

12. Apparatus according to claim 11, wherein said receiving groove has a bottom end and an open end, said open end of said can being inserted into said receiving groove through said open end of said receiving groove, said receiving groove having an annular configuration with an outer diameter and an inner diameter, said trap comprising an annular trap groove disposed adjacent to said bottom end of said receiving groove, said trap groove having an inner diameter less than the inner diameter of said receiving groove, whereby outside light entering said receiving groove is attenuated in passing through said trap groove to the interior of said can.

13. Apparatus according to claim 12, wherein said trap groove has an outer diameter equal to the inner diameter of said receiving groove.

14. Apparatus according to claim 12, wherein said trap groove is spaced from said open end of said receiving groove.

15. Apparatus according to claim 12, wherein said trap groove has a bottom end which is coplanar with the bottom end of said receiving groove.

16. Apparatus according to claim 15, wherein said trap groove has an outer end spaced from and parallel to said bottom end, said outer end of said trap groove being disposed between said bottom end and open end of said receiving groove.

* * * * *